United States Patent [19]
Diaz et al.

[11] Patent Number: 6,063,100
[45] Date of Patent: May 16, 2000

[54] EMBOLIC COIL DEPLOYMENT SYSTEM WITH IMPROVED EMBOLIC COIL

[75] Inventors: Roberto Diaz, Miami; Donald K. Jones, Lauderhill; Brett E. Naglreiter, Hollywood, all of Fla.

[73] Assignee: Cordis Corporation, Miami Lakes, Fla.

[21] Appl. No.: 09/256,163

[22] Filed: Feb. 22, 1999

Related U.S. Application Data

[60] Provisional application No. 60/077,387, Mar. 10, 1998.

[51] Int. Cl.⁷ .................................................. A61M 29/00
[52] U.S. Cl. ............................................................ 606/191
[58] Field of Search ................................... 606/191, 192, 606/194, 195, 198, 151

[56] References Cited

U.S. PATENT DOCUMENTS

| | | |
|---|---|---|
| 2,853,070 | 9/1958 | Julliard . |
| 3,334,629 | 8/1967 | Cohn . |
| 3,353,718 | 11/1967 | McLay . |
| 4,512,338 | 4/1985 | Balko et al. . |
| 4,743,230 | 5/1988 | Nordquest . |
| 4,832,692 | 5/1989 | Box et al. . |
| 4,919,121 | 4/1990 | Rydell et al. . |
| 4,994,069 | 2/1991 | Ritchart et al. . |
| 5,108,407 | 4/1992 | Geremia et al. . |
| 5,122,136 | 6/1992 | Guglielmi et al. . |
| 5,137,514 | 8/1992 | Ryan . |
| 5,168,757 | 12/1992 | Rabenau et al. . |
| 5,217,484 | 6/1993 | Marks . |
| 5,234,437 | 8/1993 | Sepetka . |
| 5,250,071 | 10/1993 | Palermo . |
| 5,261,916 | 11/1993 | Engelson . |
| 5,263,964 | 11/1993 | Purdy . |
| 5,304,195 | 4/1994 | Twyford, Jr. et al. . |
| 5,312,415 | 5/1994 | Palermo . |
| 5,334,210 | 8/1994 | Gianturco . |
| 5,336,183 | 8/1994 | Greelis et al. . |
| 5,342,304 | 8/1994 | Tacklind et al. . |
| 5,350,397 | 9/1994 | Palermo et al. . |
| 5,382,259 | 1/1995 | Phelps et al. . |
| 5,443,478 | 8/1995 | Purdy . |
| 5,470,317 | 11/1995 | Cananzey et al. . |
| 5,578,074 | 11/1996 | Mirigian . |
| 5,582,619 | 12/1996 | Ken . |
| 5,601,600 | 2/1997 | Ton .......................................... 606/191 |
| 5,609,608 | 3/1997 | Benett et al. . |
| 5,647,847 | 7/1997 | Lafontaine et al. . |
| 5,853,418 | 12/1998 | Ken et al. . |
| 5,868,753 | 2/1999 | Schatz ..................................... 606/108 |

OTHER PUBLICATIONS

Brochure entitled, "Guglielmi Detachable Coils," by Boston Scientific.
Label of IDC–18 Interlocking Detachable Coil by Target Therapeutics, Inc.
Brochure entitled, "Detachable Coil System," by Cook.
Brochure entitled, "Basix25™ Inflation Device," by Merit Medical Systems, Inc.
Brochure entitled, "MonarchAP® Inflation Device," by Merit Medical Systems, Inc.
Label of B. Braun Inflation Device Kit by B. Braun Medical Inc.

*Primary Examiner*—Michael Buiz
*Assistant Examiner*—Vy Q. Bui
*Attorney, Agent, or Firm*—Henry W. Collins

[57] ABSTRACT

A medical device for placing an embolic coil at a preselected location within a vessel comprising a positioning catheter having a distal tip for retaining the embolic coil which when pressurized with a fluid expands outwardly to release the coil at the preselected position and in which a plurality of turns at the proximal portion of the embolic coil are spot welded to adjacent turns to prevent this proximal portion of the coil from elongating or stretching while also providing a coil which is very flexible.

17 Claims, 2 Drawing Sheets

EMBOLIC COIL DEPLOYMENT SYSTEM WITH IMPROVED EMBOLIC COIL

This application claims benefit of provisional application Ser. No. 60/077,387 filed Mar. 10, 1998.

BACKGROUND OF THE INVENTION

1. Field of the Invention

The present invention relates to a medical device for placing an embolic coil at a preselected location within a vessel of the human body, and more particularly, relates to a catheter having a distal tip for retaining the embolic coil in order to transport the coil to a preselected position within the vessel and a control mechanism for releasing the embolic coil at the preselected position.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils to preselected position within vessel of the human body in order to treat aneurysms or alternatively to occlude the blood vessel at the particular location.

Coils which are placed in vessels may take the form of helically wound coils, or alternatively, may be random wound coils, coils wound within other coils or many other such coil configurations. Examples of various coil configurations are disclosed in U.S. Pat. No. 5,334,210, entitled, "Vascular Occlusion Assembly"; U.S. Pat. No. 5,382,259, entitled, "Vasoocclusion Coil With Attached Tubular Woven Or Braided Fibrous Coverings." Embolic coils are generally formed of a radiopaque metallic materials, such as platinum, gold, tungsten or alloys of these metals. Often times several coils are placed at a given location in order to occlude the flow of blood through the vessel by promoting thrombus formation at the particular location.

In the past, the proximal end of embolic coils have been placed within the distal end of the catheter and when the distal end of the catheter is properly positioned the coil may then be pushed out of the end of the catheter with, for example a guidewire, to release the coil at the desired location. This procedure of placement of the embolic coil is conducted under fluoroscopic visualization such that the movement of the coil through the vasculature of the body may be monitored and the coil may be placed in the desired location. With these placements systems there is very little control over the exact placement of the coil since the coil may be ejected to a position some distance beyond the end of the catheter. As is apparent, with these latter systems, when the coil has been released from the catheter it is difficult, if not impossible, to retrieve the coil or to reposition the coil.

Numerous procedures have been developed to enable more accurate positioning of coils within a vessel. Still another such procedure involves the use of a glue or solder for attaching the embolic coil to a guidewire which, is in turn, placed within a flexible catheter for positioning the coil within the vessel at a preselected position. Once the coil is at the desired position, the coil is restrained by the catheter and the guidewire is pulled from the proximal end of the catheter to thereby cause the coil to be detached from the guidewire and released from the catheter system. Such a coil positioning system is disclosed in U.S. Pat. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to thereby release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be too stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate element which extends throughout the length of the catheter with the resulting stiffness of the catheter.

Still another method for placing an embolic coil is disclosed in co-pending U.S. patent application Ser. No. 09/177,848, entitled "Embolic Coil Hydraulic Deployment System," filed on Oct. 21, 1998 and assigned to the same assignee as the present patent application. This patent application discloses the use of fluid pressure which is applied to the distal tip of the catheter for expanding the lumen in order to release the embolic coil.

Various embolic coil designs have been proposed for use with coil deployment systems such as the stretch resistant vasoocclusive coil disclosed in U.S. Pat. No. 5,853,418, entitled "Stretch Resistant Vaso-occlusive Coils," which discloses a helically wound coil having a polymeric stretch resisting member extending through the lumen of the coil and fixedly attached to both the distal end and the proximal end of the coil. While the stretch resisting member prevents the coil from being stretched during use, this member which extends throughout the length of the coil tends to significantly reduce the flexibility of the coil. In order to place vaso-occlusive coils into a desired location it is very important that the coil be very flexible.

SUMMARY OF THE INVENTION

The present invention is directed toward a vascular occlusive coil deployment system for use in placing an embolic coil at a preselected site within a vessel which includes an elongated, flexible catheter having a distal tip for retaining the coil so that the coil may be moved to the preselected position within the vessel. The catheter has a lumen which extends therethrough the length of the catheter and also includes a distal end which is formed of a material having a durometer such that when a fluid pressure of about 90 to 450 pounds per square inch (psi) is applied to the interior of the catheter, the walls of the distal tip expand outwardly, or radially, to thereby increase the lumen of the distal tip of the catheter. The proximal end of the embolic coil is placed into the lumen of the distal tip of the catheter and is retained by the distal tip of the catheter. A hydraulic injector, such as a syringe, is coupled to the proximal end of the catheter for applying a fluid pressure to the interior of the catheter. When the coil is placed at a desired position within a vessel, fluid pressure is then applied to the interior of the catheter by the hydraulic injector to thereby cause the walls of the distal tip to expand outwardly to thereby release the coil for placement in the vessel.

In order to prevent the proximal portion of the coil which is held by the distal tip of the coil deployment system from stretching and unwinding which could cause the premature release of the coil, the proximal portion of the coil is modified in a manner "lock" adjacent coils together to thereby prevent elongation of the proximal portion of the coil. Such elongation will result in the stretching or unwinding of the coil thereby reducing the outside diameter of the coil with the result that the coil could be prematurely released from the distal tip of the deployment system.

Accordingly, the embolic coil takes the form of a tightly wound helical coil having a distal end, a proximal end and a lumen extending therethrough also includes a seal plug disposed in fluid tight engagement within the coil lumen at the proximal end of the coil. At the proximal portion of the coil several turns of the coil are spot welded to adjacent turns to thereby prevent elongation of this proximal portion of the coil.

In accordance with another aspect of the present invention, the series of spot welded points between adjacent coils forms a straight line which is parallel to the longitudinal axis of the coil.

In accordance with another aspect of the present invention, the series of spot welded points form two straight lines both of which are parallel to the longitudinal axis of the coil.

In accordance with still another aspect of the present invention, the series of spot welded points form a helical path with respect to the longitudinal axis of the coil.

In still another aspect of the present invention, the proximal portion of the coil having turns of the coil spot welded to adjacent turns is of a length in a range of about 0.5 to 4 millimeters and the entire length of the coil is in a range of about 1.5 to 30 centimeters. Preferably, the length of the proximal portion of the coil having turns which are spot welded to adjacent turns is of a length of about 2.5 millimeters or about 1 percent of the length of the coil.

In accordance with another aspect of the present invention, the flexible catheter is comprised of a proximal section and a relatively short distal section. The proximal section is formed of a material which is sufficiently flexible to be passed through the vasculature of the human body and is of a durometer which essentially resists outward expansion when a fluid pressure on the order of about 90 to 450 psi is applied to the interior of the catheter. The distal section of the catheter is formed of a material which is also sufficiently flexible to be passed through the vasculature of the body, yet is of a durometer which is significantly lower than the durometer of the proximal section and exhibits the property of expanding outwardly, or radially, when such a fluid pressure is applied to the interior of the catheter to thereby permit the release of the embolic coil.

In accordance with still another aspect of the present invention, the distal section of the catheter has a durometer in a range of between about 25D and 55D.

In still another aspect of the present invention, the embolic coil is comprised of a helical coil having a proximal end, a distal end, and a lumen extending therethrough. A seal plug is disposed within the lumen of the proximal end of the coil in fluid-tight engagement. The proximal end of the coil is disposed in a fluid-tight engagement within the lumen of the distal section of the catheter and is retained by the lumen of the catheter for subsequent release.

In another aspect of the present invention, the hydraulic injector for applying a fluid pressure to the interior of the catheter takes the form of a syringe which is coupled to the proximal end of the catheter for, upon movement of the piston, creating a fluid pressure which is applied to the interior of the catheter to thereby cause the release of the embolic coil.

In accordance with another aspect of the present invention, the embolic coil may take the form of other types of implantable devices, such as a vascular filter.

In another aspect of the present invention, there is provided a method for placing an embolic coil with a selected site within a vessel of the body comprising the steps of advancing a catheter through the vasculature of the body to place an embolic coil which is retained within the lumen of the distal tip of the catheter to a preselected site, applying a fluid pressure to the interior of the catheter to thereby cause the distal tip of the catheter to expand radially outwardly to release the embolic coil at the preselected site, and withdrawing the catheter from the vasculature system.

These aspects of the invention and the advantages thereof will be more clearly understood from the following description and drawings of a preferred embodiment of the present invention:

DESCRIPTION OF A PREFERRED EMBODIMENT

Figure 1:
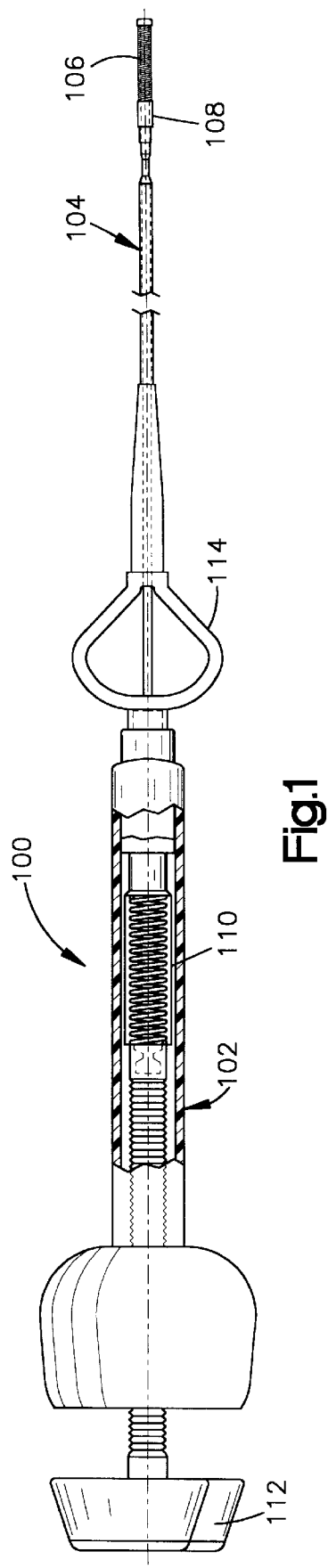
FIG. 1 is an enlarged, partially sectioned view of the hydraulic vascular occlusive coil deployment system.

FIG. 1 generally illustrates the vascular occlusive coil deployment system 100 which is comprised of a hydraulic injector or syringe 102, coupled to the proximal end of a catheter 104. An embolic coil 106 is disposed within the lumen of the distal end 108 of the catheter. The proximal end of the coil 106 is tightly held within the lumen of the distal section 108 of the catheter 104 until the deployment system is activated for release of the coil. As may be seen, the syringe 102 includes a threaded piston 110 which is controlled by a handle 112 for infusing fluid into the interior of the catheter 104. Also as illustrated, the catheter 104 includes a winged hub 114 which aids in the insertion of the catheter into the vascular system of the body.

Figure 2:
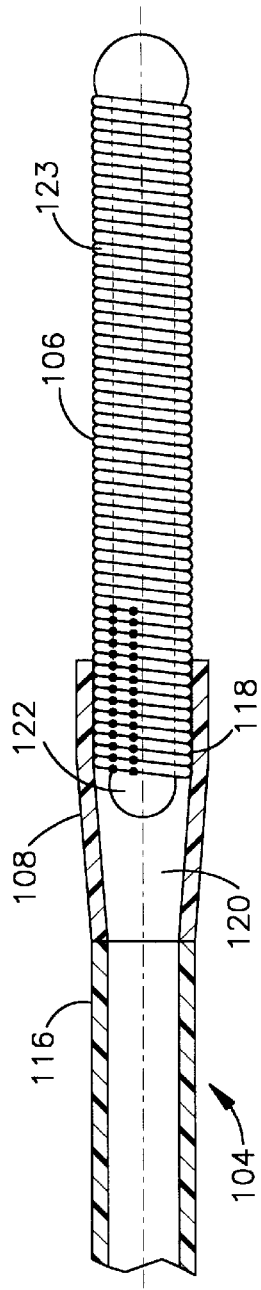
FIG. 2 is an enlarged partially sectional view showing the distal end of the coil deployment system prior to deployment of the coil including an embolic coil of the present invention having turns in the proximal portion of the coil spot welded to adjacent turns along a helical curve.

FIG. 2 illustrates in more detail the distal end of the catheter 104. The catheter 104 includes a proximal section 116 and the distal section 108. The proximal section 118 of the embolic coil 106 is disposed within the distal section 108 of the catheter and is tightly held within the lumen 120 of this distal section 108 prior to release of the coil. As may be appreciated, FIG. 2 illustrates the vascular occlusive coil deployment system prior to activation of the piston of the syringe and prior to release of the coil.

The embolic coil 106 may take various forms and configurations and may even take the form of a randomly wound coil, however, with the helical wound coil as illustrated in FIG. 2, the coil is provided with a weld bead or seal plug 122 which is disposed in a lumen 123 which lumen extends throughout the length of the coil 106. The seal plug 122 serves to prevent the flow of fluid through the lumen of the coil 106 so that when the coil 106 is placed in fluid-tight engagement with the lumen 120 the coil serves to provide a fluid-tight seal at the distal end of the catheter 104. Adjacent turns of the coil 106 at the proximal end 118 of the coil are preferably continuously welded together so that the welded turns of the coil in conjunction with the plug seal 122 provide a generally unitary structure with the coil being very flexible with the proximal end of the coil being stretch resistant. The plug seal 122 serves to plug or seal the distal end of the catheter in a fluid tight relationship.

Preferably, the proximal section 116 and the distal section 108 of the catheter 104 are formed of materials having different durometers. The proximal section 116 is preferably formed of Pebax material having a durometer in a range of about 62D to 75D. The proximal section is sufficiently flexible to transverse the vasculature of the human body, but is sufficiently rigid such that when a fluid pressure of approximately 90 to 450 psi is applied to the interior of this section of the catheter there is very little, if any, radial expansion of the walls of this section. On the other hand, the distal section 108 of the catheter is preferably formed of polymer material with a relatively low durometer which, exhibits the characteristic that when a fluid pressure of approximately 90 to 450 psi is applied to the interior of the catheter the walls of the distal section 108 expand radially, somewhat similar to the action of a balloon inflating, to thereby release the proximal end 118 of the coil 106. As may be appreciated, there are numerous materials which could be used to fabricate the proximal section 116 and distal section 108 of the catheter 104, however, the distal section 108 is preferably formed from a block copolymer such as Pebax having a durometer of between 25D and 55D with a durometer of 40D being the preferred durometer.

Figure 3:
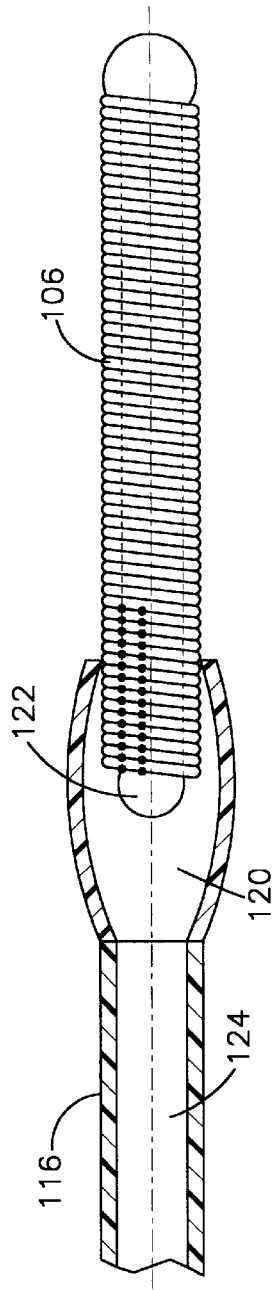
FIG. 3 and 4 illustrate the sequential steps in the radial expansion of the distal tip of the coil deployment system as the embolic coil is released.
Figure 4:
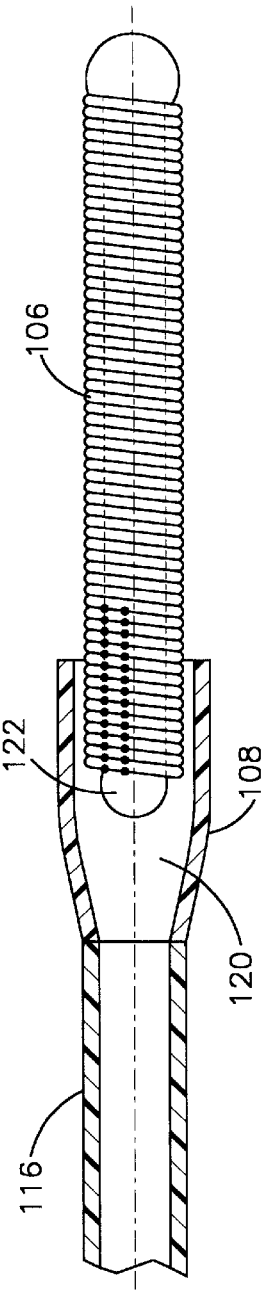

FIGS. 3 and 4 generally illustrate the coil release mechanism in action for the vascular occlusive catheter deployment system. More particularly, as shown in FIG. 3, when a hydraulic pressure is applied to the interior 124 of the catheter 104 the relatively low durometer distal section 108 of the catheter begins to expand radially, much as a balloon expands during the process of inflation. As the distal section 108 continues to expand radially there comes a point as illustrated in FIG. 4 in which the coil 106 becomes disengaged from the lumen of the distal section 108 and the coil is then released from the catheter and is deployed at that location within the vessel.

Figure 5:
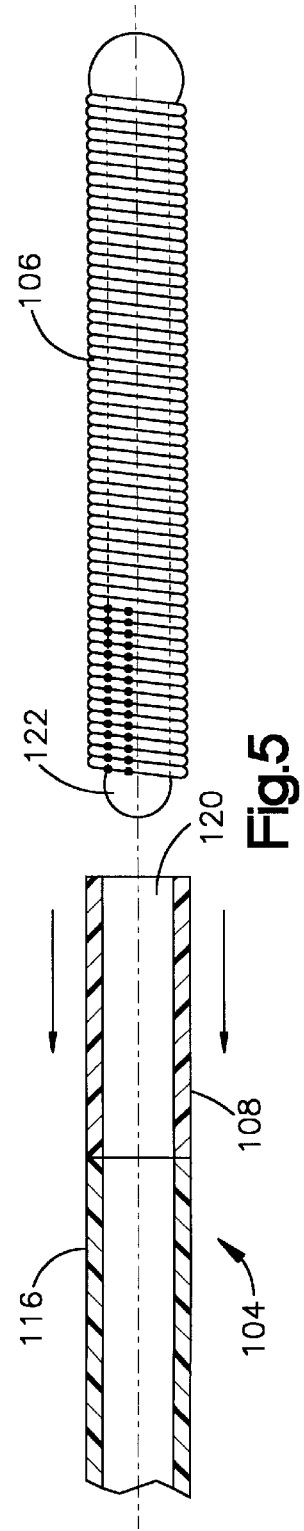
FIG. 5 illustrates the distal tip of the coil deployment system after release of the embolic coil.

As illustrated in FIG. 5, when the coil 106 has been released from the catheter 104 the catheter may then be withdrawn leaving the coil positioned at the desired site.

Figure 6:
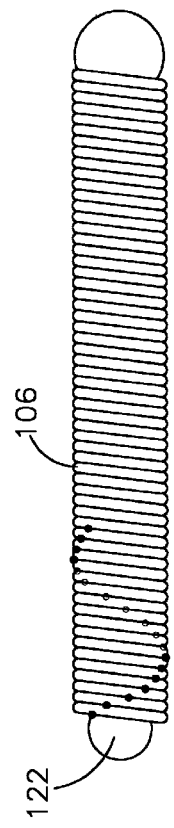
FIG. 6 is a plan view of an embolic coil having turns in the proximal portion of the coil spot welded to adjacent turns along straight lines; and, an embolic coil having coils in the proximal portion of the coil spot welded to adjacent coils along a helical line.

As illustrated in FIG. 5 and 6, the vaso-occlusion or embolic coil 106 is formed by winding a platinum alloy wire into a tightly wound helical configuration. The diameter of the wire is generally in the range of about 0.0015 to 0.008 inches. The outside diameter of the coil 106 is preferably in the range of about 0.006 to 0.055 inches. While the particular embolic coil 106 illustrated in FIG. 6 and 7 is shown as being a straight coil it should be appreciated that embolic coils take the form of various configurations and may for example, take the form of a helix, a random shape configuration or even a coil within a coil configuration.

With the embodiment of the coil deployment system disclosed in this application it may be noted that the proximal end of the embolic coil is retained or held by the distal tip of the coil deployment system as the coil is moved into a target position. Often times it is necessary to move the coil to a certain position within the vasculature and then to withdraw the coil back to a more proximal position within the vasculature. During the movement of the coil through the vasculature, particularly when the coil is withdrawn, it is possible to stretch or unwind the turns of the coil. If the turns of the coil which are held or restrained by the distal tip of the deployment catheter or stretched or unwound the result is that the outside diameter of the coil in this area decreases. With a decrease in the outside diameter of the coil in the proximal portion of the coil it is possible for the coil to be prematurely released from the deployment system.

In order to prevent such premature release caused by the stretching or unwinding of the proximal portion of the coil, adjacent turns of the proximal portion of the coil are spot welded together in order to prevent separation of these turns with the result in stretching of the coil. The length of the embolic coil is about 1.5 to about 30 centimeters and the length of the proximal portion of the coil having adjacent coils spot welded is preferably in a range of about 0.5 to 4 millimeters. In a preferred embodiment, the length of the proximal portion of the coil having adjacent turns welded together is about 2.5 millimeters.

Preferably the line of points formed by spot welding of adjacent coils forms a single line which extends generally parallel to the longitudinal axis of the coil, but the weld points may extend along two parallel lines which extend generally parallel to the longitudinal axis of the embolic coil as illustrated in FIG. 5. Alternatively, the spot welding points may be arranged to form a generally helical configuration on the outside surface of the coil with respect to the longitudinal axis of the coil as illustrated in FIG. 6.

A liquid silicon material (not shown) may be injected to fill the lumen of the proximal portion of the coil. The silicone material is then allowed to cure in order to further seal the proximal end of the coil to prevent fluid leakage through the turns of the coil. Also, as may be appreciated, instead of spot welding adjacent turns of the coil, the adjacent turns may be bonded by various other means such as, for example, by glueing or being attached by wrapping with thread.

With the coil design of the present invention the embolic coil is prevented from stretching over the proximal portion of the coil, however, the coil remains very flexible as is required for proper placement of an embolic coil.

With the vascular occlusive coil deployment system of the present invention it is possible to place an embolic coil very precisely at a desired location within a vessel. Once the coil has been placed in that location by use of the catheter, the catheter may be activated by applying a hydraulic pressure to the interior of the catheter to thereby cause the catheter to release the coil and deposit the coil very accurately at the desired location.

As is apparent, there are numerous modifications of the preferred embodiment described above which will be readily apparent to one skilled in the art, such as many variations and modifications of the coil including numerous coil winding configurations, or alternatively other types of implant devices, such as a vascular filter. Also, there are obviously variations of the syringe arrangement for applying a fluid pressure to the interior of the catheter, including many other fluid pressure generating systems for increasing the pressure within the interior of a catheter in order to cause the distal section of the catheter to expand. These modifications would be apparent to those having ordinary skill in the art to which this invention relates and are intended to be within the scope of the claims which follow.

What is claimed is:

1. A vaso-occlusive coil deployment system for use in placing a coil at a preselected site within a vessel comprising:
    an elongated flexible catheter having a lumen extending therethrough and having a proximal section and a distal section, said distal section of the catheter being formed of a material having a durometer which exhibits the characteristic that when a fluid pressure is applied to the interior of the catheter the walls of the distal section of the catheter expand outwardly;
    a syringe coupled to the proximal section of the catheter for applying a fluid pressure to the interior of the catheter to thereby cause the distal section of the catheter to expand outwardly; and,
    an embolic coil being disposed in fluid-tight engagement within the lumen of the distal section of the catheter, said coil comprising a tightly wound helical coil having a distal end, a proximal end having a proximal portion and a lumen extending therethrough, a seal plug is disposed in fluid tight engagement within the coil lumen at the proximal end of the coil, and a plurality of turns of the proximal portion of the coil are welded to an adjacent turn of the coil to prevent axial stretching of the proximal portion of the coil while retaining flexibility of the coil.

2. A vaso-occlusive coil deployment system as defined in claim 1, herein the length of the embolic coil is in a range of about 1.5 to 30 centimeters and the length of the proximal portion of the coil having turns spot welded to adjacent turns is in a range of about 0.5 to 4 millimeters.

3. A vaso-occlusive coil deployment system as defined in claim 2, wherein each of the said turns of the proximal portion of the coil are spot welded to an adjacent turn with the series of spot welded points forming a straight line which is parallel to the longitudinal axis of the coil.

4. A vaso-occlusive coil deployment system as defined in claim 2, wherein the series of spot welded points form two straight lines both of which are parallel to the longitudinal axis of the coil.

5. A vaso-occlusive coil deployment system as defined in claim 2, wherein each of the said turns of the proximal portion of the coil are spot welded to an adjacent turn with the series of spot welded points form a helical path with respect to the longitudinal axis of the coil.

6. A vaso-occlusive coil deployment system as defined in claim 1, wherein the length of the coil is in a range of about 1.5 to 30 centimeters and the length of the proximal portion of the coil having turns of the coil spot welded to an adjacent turn is in a range of about 2.5 millimeters.

7. A vaso-occlusive coil deployment system for use in placing a coil at a preselected site within a vessel comprising:
    an elongated flexible catheter having a lumen extending therethrough and having a proximal section and a distal section having a distal tip, said distal section of the catheter being formed of a material having a durometer which exhibits the characteristic that when a fluid pressure of about 90 to 450 psi applied to the interior of the catheter the walls of the distal section of the catheter expand outwardly;
    a piston coupled to the proximal section of the catheter for applying a fluid pressure to the interior of the catheter to thereby cause the distal section of the catheter to expand outwardly to thereby release the coil; and,
    an embolic coil being disposed in fluid-tight engagement within the lumen of the distal section of the catheter, said coil comprising a tightly wound helical coil having a distal end, a proximal end having a proximal portion and a lumen extending therethrough, a seal plug is disposed in fluid tight engagement within the coil lumen at the proximal end of the coil, and at least four of the turns of the proximal portion of the coil are spot welded to an adjacent turn of the coil to prevent axial stretching of the proximal portion of the coil while retaining flexibility of the remain portion of the coil.

8. A vaso-occlusive coil deployment system as defined in claim 7, herein said proximal section of said catheter is formed of a material which is sufficiently flexible to be passed through the vasculature of the body and is formed of a material which exhibits the characteristic of having substantially no radial expansion when a fluid pressure of about 90 to 450 psi is applied to the interior of the catheter, the distal tip is formed of a material which is also sufficiently flexible to be passed through the vasculature of the body and is of a durometer which is substantially lower than the durometer of the proximal section.

9. A vaso-occlusive coil deployment system as defined in claim 8, wherein the distal tip of the catheter is formed of a polymer having a durometer in a range of between about 25D and 55D.

10. A vaso-occlusive coil deployment system as defined in claim 8, wherein the distal tip of the catheter has a durometer of about 40D.

11. A vaso-occlusive coil deployment system as defined in claim 9, wherein said proximal section of said catheter is formed of a polymer having a durometer in a range of about 62D to 75D.

12. A vaso-occlusive coil deployment system for use in placing a coil at a preselected site within a vessel comprising:
    an elongated flexible catheter having a lumen extending therethrough and having a proximal section and a distal section having a distal tip, said distal section of the catheter being formed of a material having a durometer which exhibits the characteristic that when a fluid pressure of about 90 to 450 psi applied to the interior of the catheter the walls of the distal section of the catheter expand outwardly;
    a fluid pressure generating device coupled to the proximal section of the catheter for applying a fluid pressure to the interior of the catheter to thereby cause the distal section of the catheter to expand outwardly; and, an embolic coil being disposed in fluid-tight engagement within the lumen of the distal section of the catheter, said coil comprising a tightly wound helical coil having a distal end, a proximal end and a lumen extending therethrough, a seal plug is disposed in fluid tight engagement within the coil lumen at the proximal end having a proximal portion of the coil, and a plurality of the turns of the proximal portion of the coil are spot welded to an adjacent turn of the coil to prevent axial stretching of the proximal portion of the coil while retaining flexibility of the remain portion of the coil.

13. A vaso-occlusive coil deployment system as defined in claim 12, wherein the length of the embolic coil is in a range of about 1.5 to 30 centimeters and the length of the proximal portion of the coil having turns spot welded to adjacent turns is in a range of about 1 to 4 millimeters.

14. A vaso-occlusive coil deployment system as defined in claim 13, wherein said proximal section of said catheter is formed of a material which is sufficiently flexible to be passed through the vasculature of the body and is formed of a material which exhibits the characteristic of having substantially no radial expansion when a fluid pressure of about 90 to 450 psi is applied to the interior of the catheter, the distal tip is formed of a material which is also sufficiently flexible to be passed through the vasculature of the body and is of a durometer which is substantially lower than the durometer of the proximal section.

15. A vaso-occlusive coil deployment system as defined in claim 14, wherein the distal tip of the catheter is formed of a polymer having a durometer in a range of between about 25D and 55D.

16. A vaso-occlusive coil deployment system as defined in claim 14, wherein the distal tip of the catheter has a durometer of about 40D.

17. A vaso-occlusive coil deployment system for use in placing a coil at a preselected site within a vessel comprising:

an elongated flexible catheter having a lumen extending therethrough and having a proximal section and a distal section, said distal section of the catheter being formed of a material having a durometer which exhibits the characteristic that when a fluid pressure is applied to the interior of the catheter the walls of the distal section of the catheter expand outwardly;

a syringe coupled to the proximal section of the catheter for applying a fluid pressure to the interior of the catheter to thereby cause the distal section of the catheter to expand outwardly; and, an embolic coil being disposed in fluid-tight engagement within the lumen of the distal section of the catheter, said coil comprising a tightly wound helical coil having a distal end, a proximal end having a proximal portion and a lumen extending therethrough, a seal plug is disposed in fluid tight engagement within the coil lumen at the proximal end of the coil, and a plurality of turns of the proximal portion of the coil are bonded to an adjacent turn of the coil to prevent axial stretching of the proximal portion of the coil while retaining flexibility of the coil.

* * * * *